US007118535B2

(12) United States Patent
Sawanoi et al.

(10) Patent No.: US 7,118,535 B2
(45) Date of Patent: Oct. 10, 2006

(54) ELECTRONIC BLOOD PRESSURE MEASUREMENT DEVICE AND BLOOD PRESSURE MEASURING METHOD

(75) Inventors: Yukiya Sawanoi, Nara (JP); Takahide Tanaka, Otsu (JP); Hiroya Nakanishi, Kyoto (JP); Takefumi Nakanishi, Nagaokakyo (JP); Yoshihiko Sano, Kyoto (JP); Minoru Taniguchi, Uji (JP); Tomonori Inoue, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/103,506

(22) Filed: Apr. 12, 2005

(65) Prior Publication Data
US 2005/0234350 A1 Oct. 20, 2005

(30) Foreign Application Priority Data
Apr. 20, 2004 (JP) ............................. 2004-123857

(51) Int. Cl.
    *A61B 5/02* (2006.01)
    *A61B 5/103* (2006.01)
    *A61B 5/117* (2006.01)
    *A61B 1/00* (2006.01)

(52) U.S. Cl. .................... 600/490; 600/587; 33/512
(58) Field of Classification Search ........ 600/490–503, 600/587, 595; 33/511, 512
See application file for complete search history.

(56) References Cited

U.S. PATENT DOCUMENTS 3,812,844 A * 5/1974 Sokol .......................... 600/499
4,429,699 A 2/1984 Hatschek
6,228,035 B1 * 5/2001 Packman et al. ............ 600/485
6,719,712 B1 * 4/2004 Zigmont ...................... 602/19
7,008,379 B1 * 3/2006 Takahashi et al. .......... 600/490
2004/0127801 A1 7/2004 Takahashi et al.

FOREIGN PATENT DOCUMENTS

| DE | 3426183 A1 | 2/1986 |
| EP | 0696433 A1 | 2/1996 |
| JP | 61-016730 A | 1/1986 |
| JP | 61-048339 A | 3/1986 |
| JP | 63-186625 A | 8/1988 |
| JP | 06-237906 | 8/1994 |
| JP | 06-245911 | 9/1994 |
| JP | 07-059740 | 3/1995 |
| JP | 2004-154458 A | 6/2004 |

OTHER PUBLICATIONS

European Search Report dated Jul. 27, 2005, directed to counterpart foreign application.

* cited by examiner

*Primary Examiner*—Charles A Marmor, II
*Assistant Examiner*—Navin Natnithithadha
(74) *Attorney, Agent, or Firm*—Morrison & Foerster LLP

(57) ABSTRACT

Prior to blood pressure calculations, air is enclosed in a blood pressure measurement bladder to be wound and mounted around the region for measurement, in advance. By referring to the variation in the pressure therein, the circumferential length of the region for measurement is detected based on the variation in the pressure therein during the winding correction determination process for the region for measurement. Then, the process enters blood pressure measurement, and the blood pressure measurement bladder is pressurized or depressurized. The pressure in the blood pressure measurement bladder is detected. A blood pressure based on the detected pressure is calculated according to the circumferential length of the region for measurement which has been detected in advance.

9 Claims, 11 Drawing Sheets

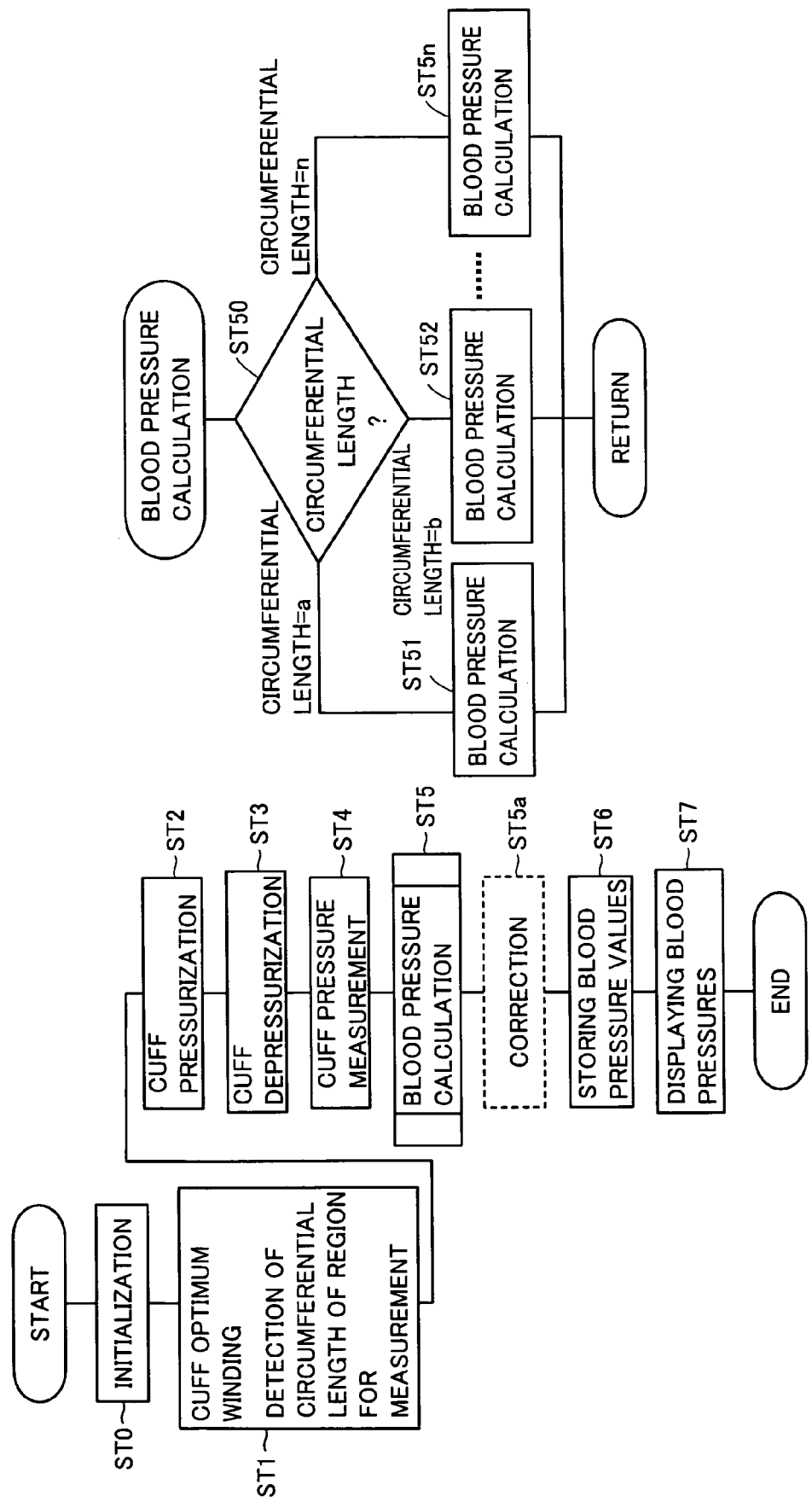

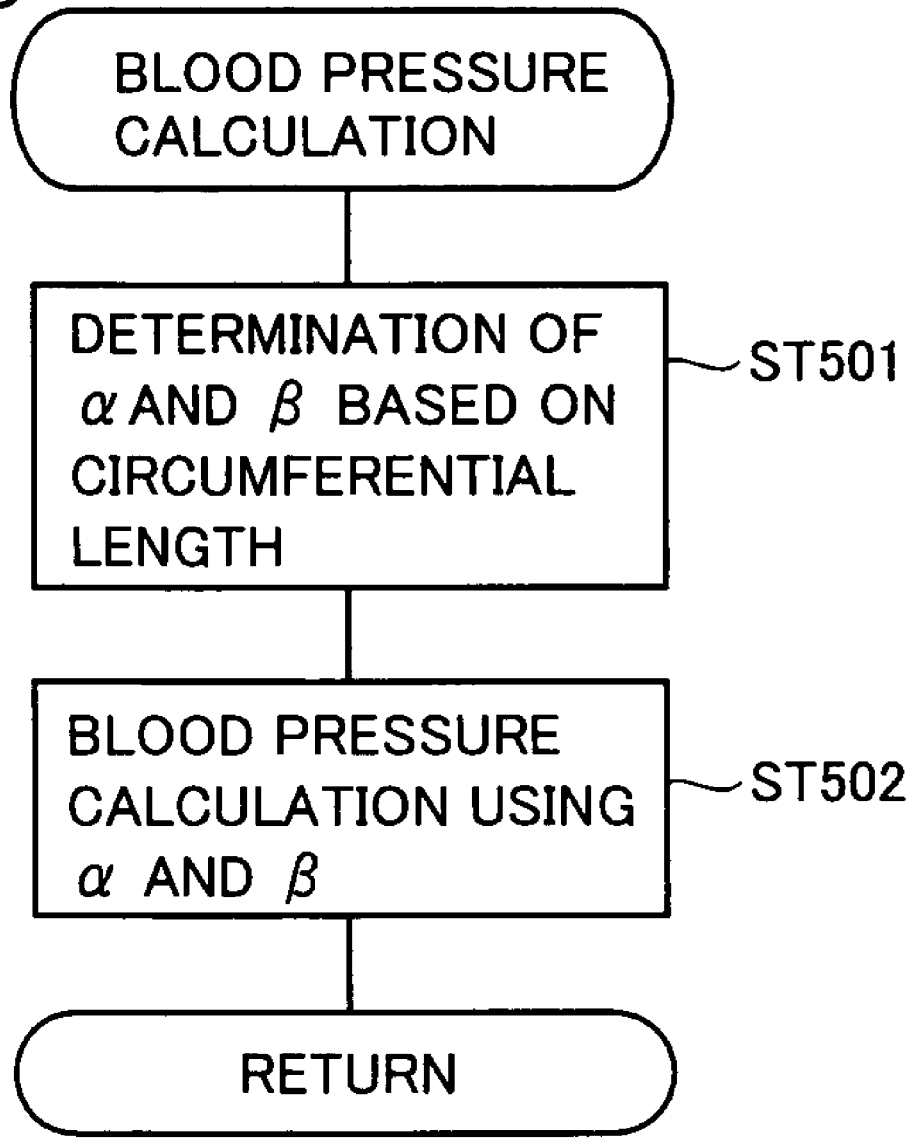

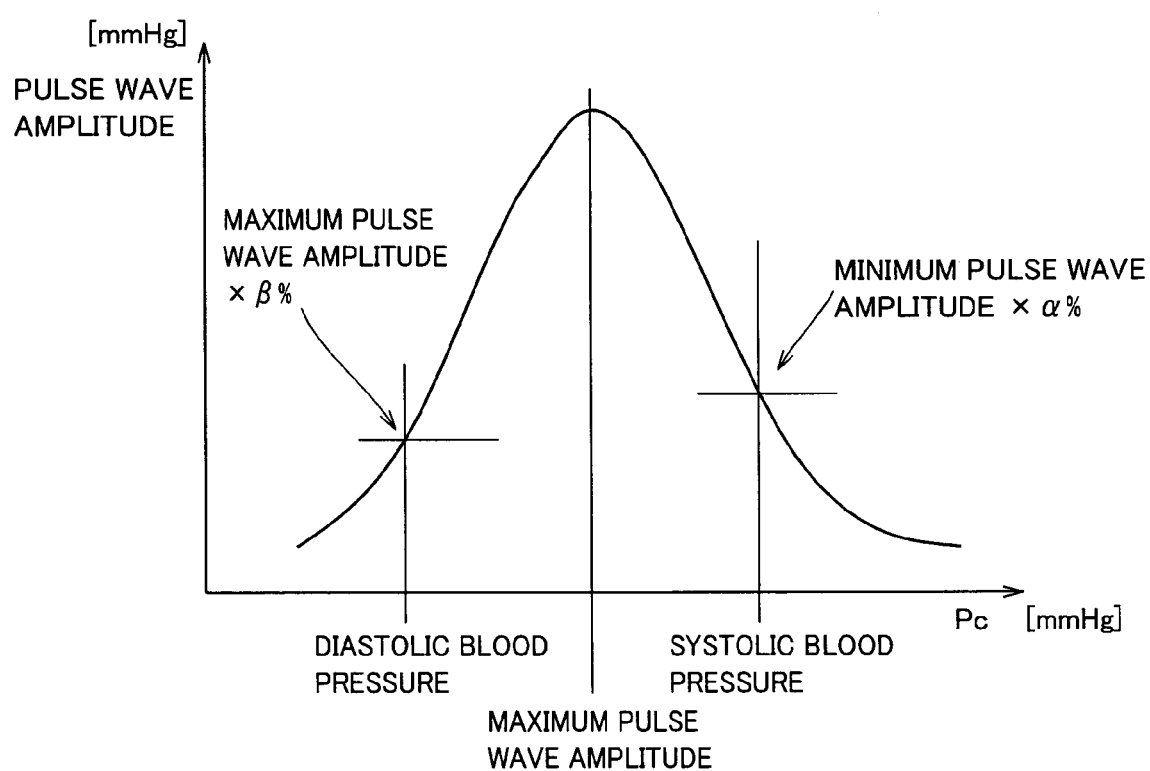

ELECTRONIC BLOOD PRESSURE MEASUREMENT DEVICE AND BLOOD PRESSURE MEASURING METHOD

BACKGROUND OF THE INVENTION

1. Field of the Invention

The present invention relates to an electronic blood pressure measurement device and blood pressure measuring method for measuring blood pressures by wrapping a bladder around a region of a living body. More particularly, the present invention relates to an electronic blood pressure measurement device and blood pressure measuring method which detect the circumferential length of the region for measurement around which an bladder is to be wound.

2. Description of the Background Art

There has existed a conventional electronic blood pressure measurement device as follows. A user winds a cuff enclosing a bladder which is inflated when supplied with fluid such as air around a region for measurement, and then the region for measurement is pressurized or depressurized through the inflation of the bladder. Then, the blood pressure is calculated using a predetermined algorithm based on the pressure within the bladder (cuff pressure) and pulse wave signals acquired at this time. Some blood pressure measurement devices utilize Korotkoff sound instead of pulse wave signals.

However, with such a conventional electronic blood pressure measurement device, it has been difficult to automatically detect the circumferential length of the region for measurement of the user, around which the cuff is to be wound. Therefore, there has been a problem that the accuracy of blood pressure calculation varies depending on the circumferential length of the region for measurement. This is because the accuracy of blood pressure calculation is significantly affected by the relationship between the width of the cuff and the circumferential length of the region for measurement. In order to calculate accurate blood pressure values, it is necessary to press the artery in the region for measurement with an appropriate pressure. In the case where the force for pressing the artery (hereinafter, referred to as a pressing force) is either too large or too small, it is impossible to calculate accurate blood pressure values. In order to provide an appropriate pressing force, it is necessary to employ a cuff with an appropriate width for each circumferential length of the region for measurement.

On the other hand, the cuff is generally configured to have a width applicable to a certain range of circumferential lengths of the region for measurement. Therefore, for some circumferential lengths of the region for measurement, estimated accuracy of blood pressure measurement can not be achieved. Therefore, it is desired to employ a blood pressure measurement process appropriate for the circumferential length of the region for measurement. There have been suggested some conventional blood pressure measurement devices and methods which prepare and selectively employ several types of blood pressure calculation algorisms based on the characteristics of the pulse wave amplitude or the characteristics of Korotkoff sound. However, they have not covered the influences of the circumferential length of the region for measurement.

Therefore, Japanese Laid-Open Patent Publication No. 6-245911 suggested a function of detecting the circumferential length of the region for measurement. This publication suggested a function of inputting the circumferential length from outside, a function of detecting the circumferential length from the value of slide resistance provided in the cuff, and a function of detecting the circumferential length from the time required for raising the pressure within the cuff to a certain level.

The method which inputs the circumferential length from the outside, disclosed in the aforementioned publication, requires the subject to measure and detect the circumferential length in advance and also requires the subject to input the circumferential length every time he performs blood pressure measurement, thus having poor operability. Further, there will be variations in the detected circumferential length depending on the winding condition of the cuff, such as loose winding or tight winding. Therefore, the method using slide resistance or a required time period has not been regarded as a method capable of detecting an accurate circumferential length.

SUMMARY OF THE INVENTION

It is an object of the present invention to provide an electronic blood pressure measurement device and blood pressure measuring method capable of accurately detecting the circumferential length of a region for measurement.

It is another object of the present invention to provide an electronic blood pressure measurement device and blood pressure measuring method which enable accurate blood pressure measurements regardless of the circumferential length of a region for measurement.

An electronic blood pressure measurement device according to an aspect of the present invention includes a blood pressure calculation portion for calculating a blood pressure value based on the pressure in a measurement bladder which is inflated when supplied with fluid and is intended to be wound around a region for measurement according to the circumferential length of the region for measurement, and a circumferential length detection portion for detecting the circumferential length of the region for measurement based on a relative variation in the pressure in the measurement bladder during winding the measurement bladder around the region for measurement after a predetermined amount of fluid has been supplied to and enclosed in the measurement bladder for winding.

Therefore, the circumferential length of the region for measurement used for calculating a blood pressure based on the pressure in the measurement bladder can be detected based on a relative variation in the pressure in the measurement bladder during winding the measurement bladder around the region for measurement. Therefore, the circumferential length can be accurately detected, regardless of the tightness or looseness of winding of the measurement bladder.

Preferably, the circumferential length detection portion detects the circumferential length of the region for measurement, based on the time period required for raising the difference between the pressure in the measurement bladder when the measurement bladder is wound around the region for measurement after fluid has been enclosed in the measurement bladder and the pressure which is sequentially detected during further winding the measurement bladder around the region for measurement to a predetermined value.

Therefore, since the circumferential length can be detected based on the time period required for raising the difference between the pressure in the measurement bladder when the measurement bladder is wound and mounted around the region for measurement and the pressures in the measurement bladder during the subsequent winding process to a predetermined value, namely based on a relative pressure variation, the circumferential length can be accurately detected, regardless of the tightness or looseness of winding of the measurement bladder.

Preferably, the predetermined value is a value indicating a state where the measurement bladder has been optimally wound around the region for measurement. Therefore, the circumferential length can be detected at a state where the measurement bladder is optimally wound around the region for measurement, thus enabling accurate detection of the circumferential length.

Preferably, the circumferential length detection portion detects the circumferential length of the region for measurement, based on the difference between the pressure in the measurement bladder when the measurement bladder is wound around the region for measurement after fluid has been enclosed in the measurement bladder and the pressure in the measurement bladder which is detected at a predetermined time during further winding the measurement bladder around the region for measurement.

Therefore, since the circumferential length can be detected based on the difference between the pressure in the measurement bladder when the measurement bladder is wound and mounted around the region for measurement and the pressures in the measurement bladder at a predetermined time during the subsequent winding process, namely based on a relative pressure variation, the circumferential length can be accurately detected, regardless of the tightness or looseness of winding of the measurement bladder.

Preferably, the blood pressure calculation portion calculates a blood pressure value based on the pressure in the measurement bladder according to a process selected based on the circumferential length detected by the circumferential length detection portion out of a plurality of processes for calculating the blood pressure value.

Therefore, the process for blood pressure calculation can be selectively switched based on the detected circumferential length, thus enabling accurate calculation of blood pressures regardless of the circumferential length of the region for measurement.

Preferably, the blood pressure calculation portion calculates a blood pressure value based on the pressure in the measurement bladder, according to characteristic amounts for blood pressure calculation selected based on the circumferential length detected by the circumferential length detection portion.

Therefore, the characteristic amounts for blood pressure calculation can be selectively switched based on the detected circumferential length, thus enabling accurate calculation of blood pressures regardless of the circumferential length of the region for measurement.

Preferably, the blood pressure calculation portion corrects the calculated blood pressure value, according to a correction parameter value appropriate for the circumferential length detected by the circumferential length detection portion.

Therefore, the parameter value for correcting the calculated blood pressure can be selectively switched based on the detected circumferential length, thus enabling providing accurate calculated blood pressures regardless of the circumferential length of the region for measurement.

Preferably, the device further includes a pressure adjustment portion for adjusting the pressure in the measurement bladder for calculating a blood pressure value, and the pressure adjustment portion adjusts the pressure in the measurement bladder according to an adjustment parameter value appropriate for the circumferential length detected by the circumferential length detection portion.

Therefore, in adjusting the pressure in the measurement bladder for blood pressure calculation, the parameter value for adjustment can be selectively switched based on the detected circumferential length. Thus, the pressure adjustment can be made correct, thus enabling accurate calculation of blood pressures regardless of the circumferential length of the region for measurement.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 1A, 1B and 1C are an overall flowchart and flowcharts of blood pressure calculation according to the present embodiment;

FIG. 7 is a view for describing an exemplary switching of blood pressure calculation processes applied for the present embodiment of the present invention;

DESCRIPTION OF THE PREFERRED EMBODIMENTS

Hereinafter, embodiments of the present invention will be described with reference to the drawings. An electronic blood pressure measurement device according to the present embodiment may utilize either a blood-pressure measuring method according to the oscillometric method or a measuring method using Korotkoff sound.

Further, it is assumed, herein, that the region for measurement is an arm. However, the region for measurement is not limited to an arm and may be other regions such as a finger or a wrist.

Further, it is assumed that the electronic blood pressure measurement device according to the present embodiment is an electronic blood pressure measurement device in which a cuff is automatically wound around the region for measurement. Such an automatically-winding type blood-pressure measurement device may be a blood-pressure measurement device which increases the tension in the cuff to decrease the winding size thereof in a radial direction around the region for measurement by the rotation of a motor, as disclosed in Japanese Laid-Open Patent Publication No. 6-237906. Also, it may be a blood pressure measurement device which decreases the winding size of a blood-pressure measurement bladder in a radial direction around the region for measurement by the inflation force of a pressing-securing bladder through a curled elastic member, as described in the present embodiment.

Figure 2:
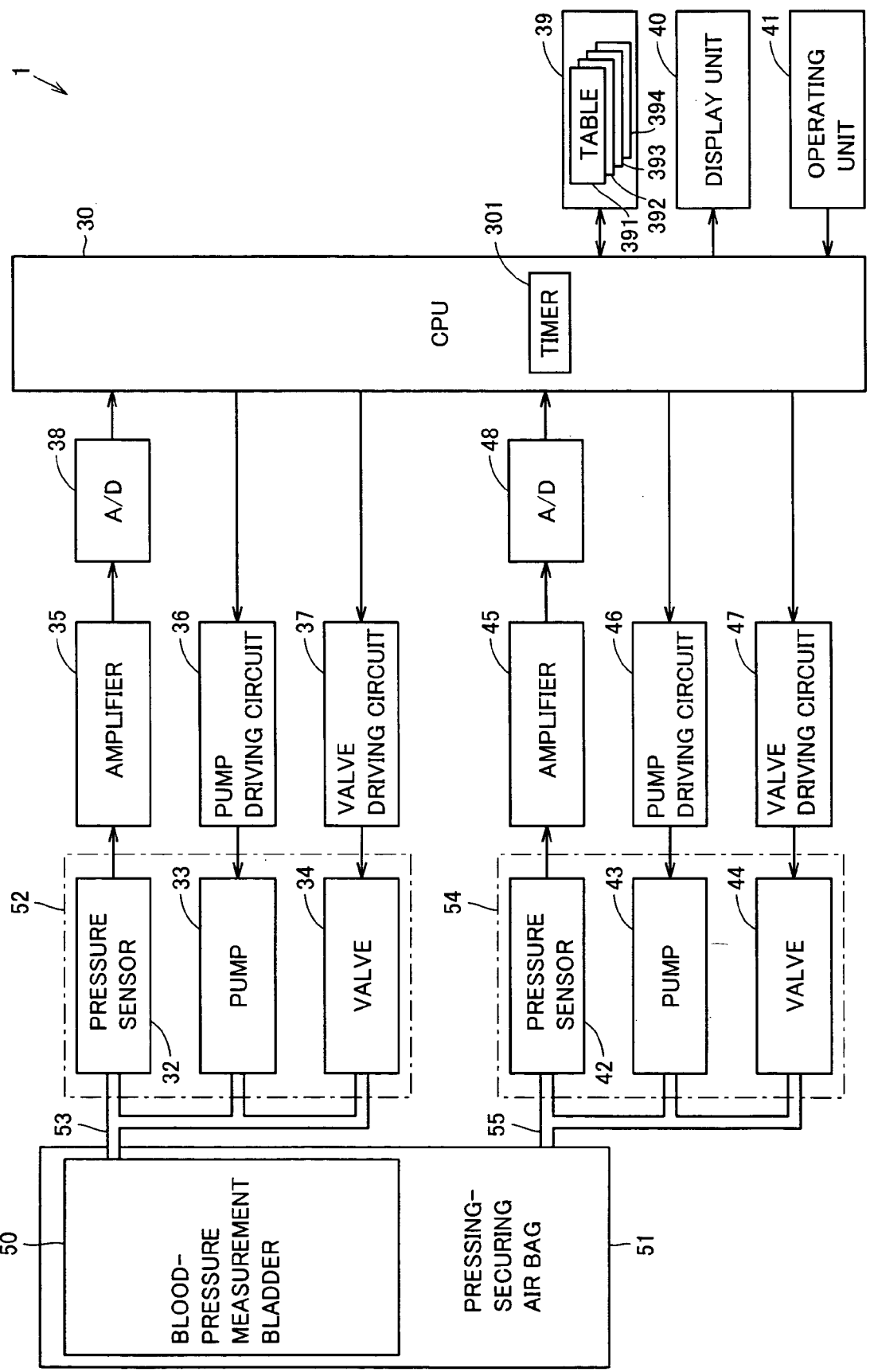
FIG. 2 is a block diagram of an electronic blood pressure measurement device applied for the present embodiment of the present invention.
Figure 3:
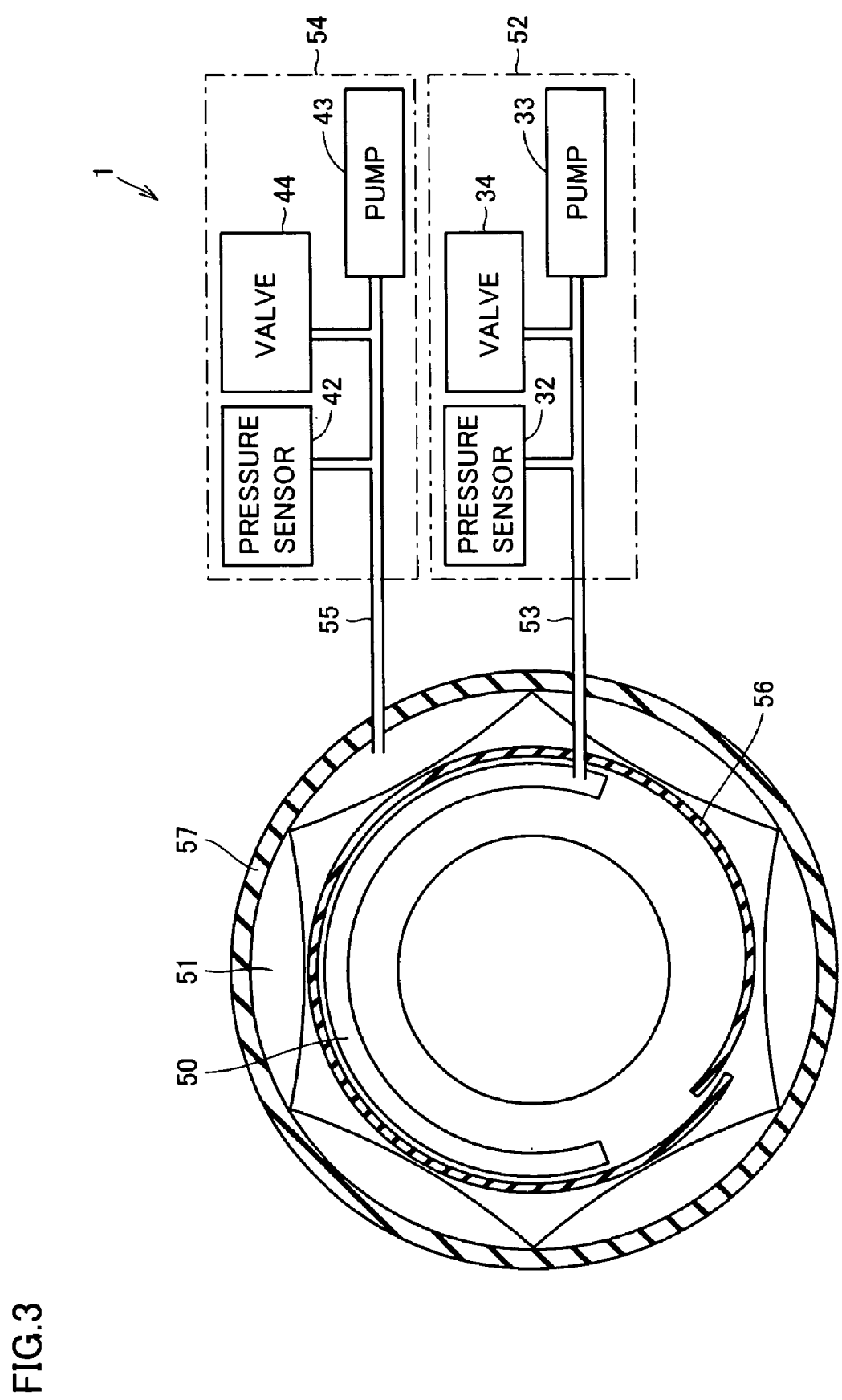
FIG. 3 is a block diagram of an air system of the electronic blood pressure measurement device applied for the present embodiment of the present invention.
Figure 4A:
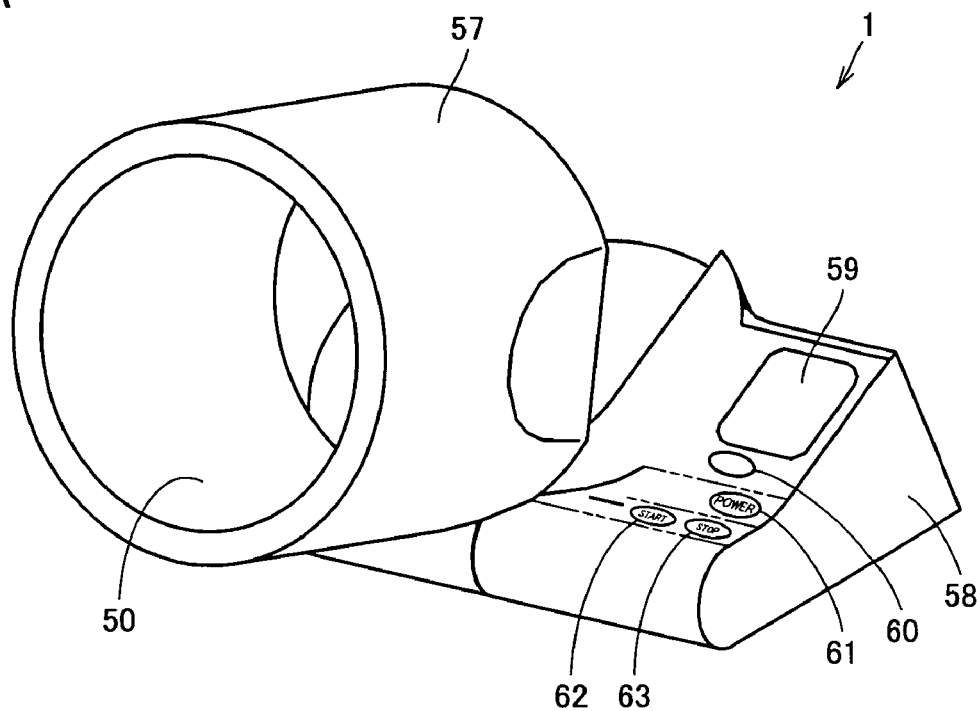
FIGS. 4A and 4B are views schematically illustrating the outward appearance and the used state of the electronic blood pressure measurement device applied for the present embodiment of the present invention.
Figure 4B:
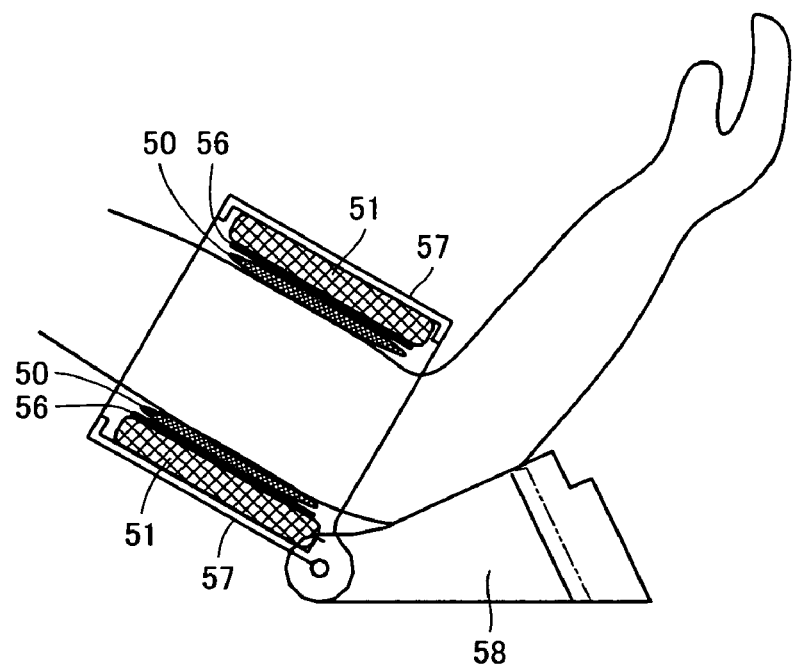

FIG. 1A, FIG. 1B, FIG. 1C, FIG. 9A and FIG. 9B illustrate flowcharts relating to blood pressure measurements. FIG. 2 illustrates a block structure of an electronic blood pressure measurement device applied to the present embodiment. FIG. 3 illustrates an air system of the electronic blood pressure measurement device and FIG. 4A and FIG. 4B schematically illustrate the outward appearance and the used state of the electronic blood pressure measurement device.

(Device Configuration)

Referring to FIG. 2, an electronic blood pressure measurement device 1 includes a blood pressure measurement bladder 50, a pressing-securing air bag 51, a blood pressure measurement air system 52 for inflating or deflating blood pressure measurement bladder 50 through a tube 53, an amplifier 35, a pump driving circuit 36, a valve driving circuit 37 and an A/D (Analog/Digital) converter 38 provided in relation to blood-pressure measurement air system 52. Further, electronic blood pressure measurement device 1 includes a pressing-securing air system 54 for inflating or deflating pressing-securing air bag 51 through a tube 55, an amplifier 45, a pump driving circuit 46, a valve driving circuit 47 and an A/D converter 48 provided in relation to pressing-securing air system 54. Electronic blood pressure measurement device 1 further includes a CPU (Central Processing Unit) 30 for centrally controlling and monitoring the respective sections, a memory 39 for storing various information such as programs for causing CPU 30 to execute predetermined operations or measured blood pressure values, a display unit 40 for displaying various information including the results of blood-pressure measurements, and an operating unit 41 which is operated for inputting various instructions for measurements. In memory 39, there are prestored programs according to the flowcharts of FIGS. 1A to 1C, FIG. 9A and FIG. 9B. These programs are read out from memory 39 and executed by CPU 30.

Blood pressure air system 52 includes a pressure sensor 32 for detecting and outputting the pressure in blood pressure measurement bladder 50 (hereinafter, referred to as a cuff pressure Pc), a pump 33 for inflating blood-pressure measurement bladder 50, and a valve 34 which is opened or closed in order to deflate blood-pressure measurement bladder 50 or enclose air in blood-pressure measurement bladder 50. Amplifier 35 receives and amplifies output signals from pressure sensor 32 and outputs them to A/D converter 38. A/D converter 38 receives the output analog signals, converts them into digital signals and outputs the converted signals to CPU 30. Pump driving circuit 36 controls the driving of pump 33 based on control signals from CPU 30. Valve driving circuit 37 executes the opening/closing control for valve 34 based on control signals from CPU 30.

Pressing-securing air system 54 includes a pressure sensor 42 for detecting and outputting the pressure in pressing-securing air bag 51, a pump 43 for inflating pressing-securing air bag 51, and a valve 44 which is opened or closed in order to discharge or enclose air from or in pressing-securing air bag 51. Amplifier 45 receives and amplifies output signals from pressure sensor 42 and outputs them to A/D converter 48. A/D converter 48 receives the output analog signals, converts them into digital signals and outputs the converted signals to CPU 30. Pump driving circuit 46 controls the driving of pump 43 based on control signals from CPU 30. Valve driving circuit 47 executes the opening/closing control for valve 44 based on control signals from CPU 30.

Referring to FIG. 4A, electronic blood pressure measurement device 1 includes a securing cylindrical case 57 for securing the arm which is the region for measurement of the subject and a blood-pressure measurement device main portion 58. Blood-pressure measurement device main portion 58 includes an LCD (Liquid Crystal Display) 59 and a lamp 60 as display device 40. Blood pressure measurement device main portion 58 further includes a power-supply switch 61, a start switch 62 and a stop switch 63 for dictating the start and the stop of blood-pressure measurement, as operating portion 41, in order to enable external operation. Securing cylindrical case 57 includes, on the inner surface thereof, blood-pressure measurement bladder 50 to be mounted around the region for measurement. FIG. 4B illustrates a state where the arm which is the region for measurement of the subject is inserted through securing cylindrical case 57 from the front side thereof in the figure.

FIG. 3 schematically illustrates a cross sectional view of securing cylindrical case 57 at the state illustrated in FIG. 4B. Securing cylindrical case 57 is provided with measurement bladder 50, a pressing-securing curled elastic member 56 the size of which in a radial direction is expansible, and pressing-securing air bag 51, from the outer circumference of the arm which is the region for measurement toward the inner surface of securing cylindrical case 57. When pressing-securing air bag 51 is inflated with air through pressing-securing air system 54 to be inflated, the size of pressing-securing curled elastic member 56 in a radial direction is decreased by the effect thereof, which causes measurement bladder 50 interposed between pressing-securing curled elastic member 56 and the human body (arm) to be pressed against the region for measurement. Thus, measurement bladder 50 is wound around the human body (arm) through pressing-securing curled elastic member 56 and pressing-securing air bag 51, thereby enabling blood-pressure measurements.

It is assumed that, in a cuff optimum winding process which will be described later, pump 43 is driven while pump 33 is maintained at a stop and thus pressing-securing air bag 51 is gradually supplied with air and is inflated, thus causing measurement bladder 50 to be wound around the arm.

(Blood Pressure Measurement Process)

In the process of FIG. 1A and FIG. 1B, blood-pressure measurement bladder 50 which is a cuff is wound around the region for measurement through the inflation of pressing-securing air bag 51. When an optimum winding condition is achieved, namely when the cuff pressure Pc in blood-pressure measurement bladder 50 reaches a predetermined level for circumferential length detection, the circumferential length of the region for measurement is acquired. Then, based on the acquired circumferential length, an optimum calculation process is selected to improve the accuracy of the blood-pressure measurements. The general outlines of the process will be described with reference to FIG. 1A.

First, at the state of FIG. 4B where blood-pressure measurements can be conducted, when the subject turns on the power supply by operating power-supply switch 61 of electronic blood pressure measurement device 1, electronic blood pressure measurement device 1 is initialized (step ST0).

In the aforementioned initialization, resetting of CPU 30, clearing of the working area of memory 39, opening of valves 34, 44, and zero-point adjustment of pressure sensors 32, 42 (adjustment to 0 mmHg) are performed. Therefore, the internal pressures of blood-pressure measurement bladder 50 and pressing-securing air bag 51 are both made to be an atmospheric pressure (0 mmHg).

Next, the subject operates start switch 62 and, when an optimum winding state of blood-pressure measurement bladder 50 is achieved, CPU 30 detects the circumferential length of the region for measurement (step ST1). The details thereof will be described later.

When the circumferential length of the region for measurement has been detected, then CPU 30 stops pump 43 which has been driven and starts the driving of pump 33, thereby gradually raising the cuff pressure Pc in blood-pressure measurement bladder 50 (step ST2). During gradually raising the pressure, when the cuff pressure Pc reaches a predetermined level for blood-pressure measurement, CPU 30 stops pump 33 and then gradually opens valve 34 which has been closed to deflate blood-pressure measurement bladder 50, thereby gradually reducing the cuff pressure Pc (step ST3). In the present embodiment, the blood pressure is measured during this slow depressurization of the cuff pressure Pc.

During gradually reducing the cuff pressure Pc, CPU 30 acquires detection signals of the cuff pressure Pc output from pressure sensor 52 at first and detects pulse wave signals superimposed on the signals (step ST4). The processes in step ST2 to step ST4 are well-known processes and are not described in detail.

Next, based on the pulse wave signals determined in step ST4, CPU 30 calculates the values of blood pressures (a systolic blood pressure, a diastolic blood pressure and a mean blood pressure) (step ST5). In the calculation of blood pressure values, a suitable algorism for calculation of blood pressure values is selectively activated based on the circumferential length of the region for measurement which has been detected in step ST1. The details thereof will be described later. Also, the blood pressure values calculated in step ST5 may be corrected (step ST5a), as will be described later.

When blood pressure values have been calculated in step ST5, CPU 30 stores the calculated blood pressure values in memory 39 (step ST6) and displays the calculated blood pressure values on LCD 59 (step ST7). At this time, valves 34 and 44 are fully opened. As described above, a series of blood pressure measurements are completed. In the case where a correction has been made in step ST5a, the corrected blood pressure values are stored in memory 39.

(Detection of Circumferential Length of Region for Measurement)

In step ST1, at first, blood-pressure measurement bladder 50 is per-pressurized according to the following process. CPU 30 closes valve 34 and drives pump 33 to supply, to blood-pressure measurement bladder 50, a predetermined amount of air which will raise the cuff pressure Pc to a pressure level enabling an optimum winding determination which will be described later, such as a level equivalent to an atmospheric pressure. Then, CPU 30 stops pump 33. The predetermined amount is a small amount and is empirically determined in advance. Further, the predetermined amount will vary depending on the size of blood-pressure measurement bladder 50, such as the volumetric capacity thereof. Subsequently, an optimum winding determination process is executed. Data indicating the predetermined amount is prestored in a memory, not shown, in CPU 30.

In the optimum winding determination process, CPU 30 closes valve 44 and drives pump 43 to gradually supply a certain amount of air to pressing-securing air bag 51 per unit time. This reduces the size of securing curled elastic member 56 in a radial direction through the inflation force of pressing-securing air bag 51, thereby pressing and securing measurement bladder 50 such that it is gradually wound around the arm which is the region for measurement. In parallel therewith, CPU 30 determines whether or not blood-pressure measurement bladder 50 has been wound around the region for measurement with a suitable pressure for blood-pressure measurement, based on the cuff pressure Pc indicated by detection signals which are sequentially output from pressure sensor 32. When it is determined that blood-pressure measurement bladder 50 has been optimally wound around the region for measurement of the subject, CPU 30 stops pump 43 and detects the circumferential length of the region for measurement.

Hereinafter, there will be described the optimum winding determination process and first and second concrete exemplary processes for detecting the circumferential length of the region for measurement.

(First Exemplary Detection Process)

Figure 5A:
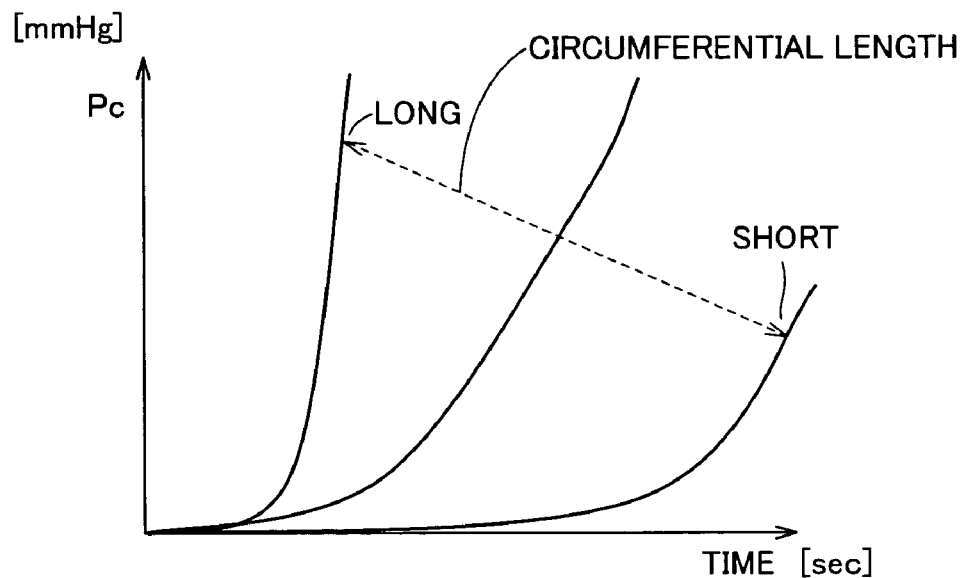
FIGS. 5A and 5B are views for describing an example of the circumferential length detection process applied for the present embodiment of the present invention.
Figure 5B:
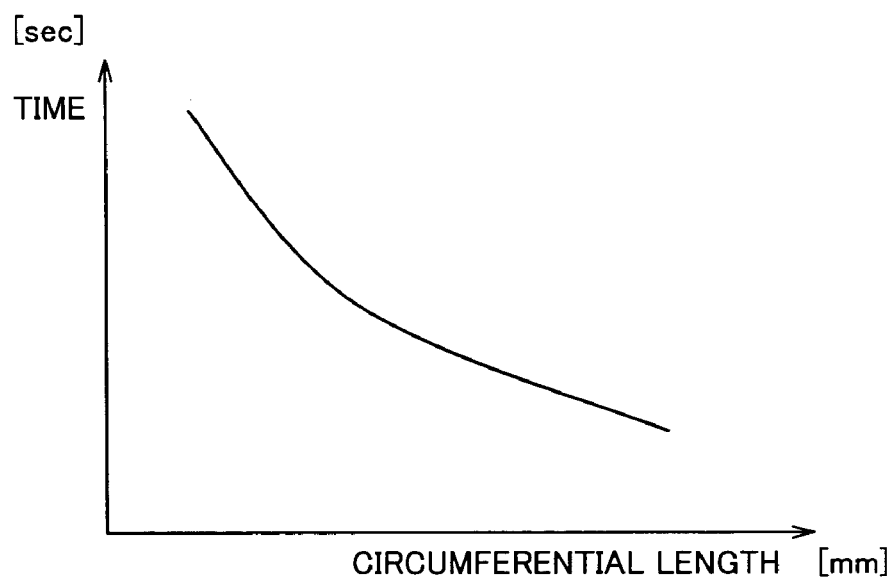

With reference to FIG. 5A and FIG. 5B, there will be described that the circumferential length of the region for measurement is determined based on the time required for raising the variation (difference) in the cuff pressure Pc since the start of winding, namely the completion of the pre-pressurization, to a predetermined value (for example, 20 mmHg), during winding of the cuff. In FIG. 5A, there is illustrated the variation in the cuff pressure Pc in relation to the circumferential length of the region for measurement designated by a dot line arrow.

In FIG. 5A, the vertical axis represents the cuff pressure Pc and the horizontal axis represents the time elapsed since the start of driving of pump 43 (start of winding) which is the elapsed time in the optimum winding determination process. As illustrated, during pressurizing and inflating pressing-securing air bag 51 after the pre-pressurization, the larger (or longer) the circumferential length of the arm (the thicker the arm), the more steeply the cuff pressure Pc rises, while the smaller (or shorter) the circumferential length of the arm (the thinner the arm), the more slowly the cuff pressure Pc rises. This is because, in the case where the arm is thicker, blood pressure measurement bladder 50 is already subjected to a high pressure by the region for measurement at the start of winding (namely, at the completion of the pre-pressurization), thereby shortening the time required for raising the cuff pressure Pc, while the opposite phenomenon occurs in the case where the arm is thinner.

In the cuff winding process illustrated in FIG. 5A, CPU 30 monitors the variation in cuff pressure Pc and, when the variation in cuff pressure Pc since the start of winding reaches a predetermined value, CPU 30 determines that the optimum winding state is achieved. Data indicating the predetermined value of variation is prestored in a memory, not shown, in CPU 30. In FIG. 5B, the vertical axis represents the time required for causing the variation in the cuff pressure Pc to satisfy (reach) the predetermined value (the time elapsed since the start of winding), and the horizontal axis represents the circumferential length of the region for measurement. It is assumed that information indicating the relationship of FIG. 5B is acquired in advance by experiments and is prestored in memory 39 as a table 391.

CPU 30 measures, using a timer 301 therein, the time required for raising the relative variation in the cuff pressure Pc to the predetermined value since the start of winding. Further, based on the measured time, CPU 30 identifies a corresponding circumferential length of the region for measurement by searching table 391 and then reads out it therefrom. Thus, the circumferential length of the region for measurement of the subject can be detected (determined) at the cuff optimum winding state.

While the circumferential length of the region for measurement is detected by searching table 391 herein, the circumferential length of the region for measurement may be calculated using an equation representing the relationship of FIG. 5B.

(Second Exemplary Detection Process)

Figure 6A:
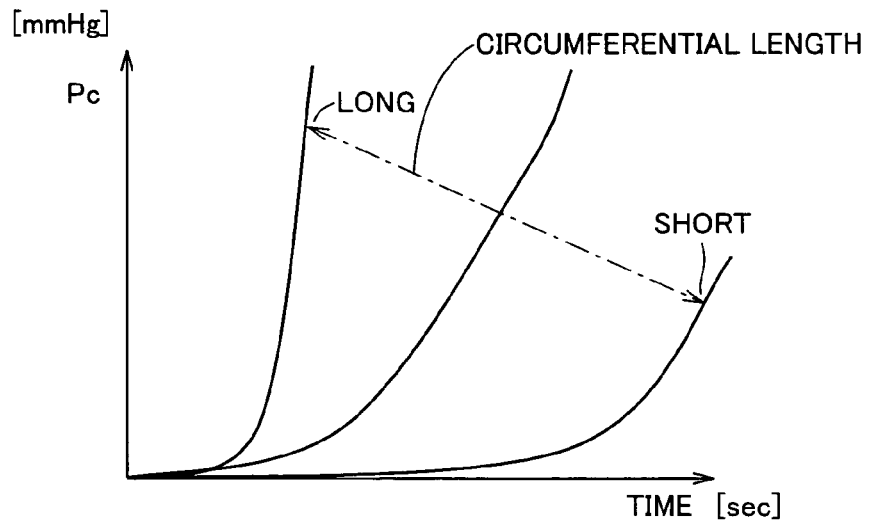
FIG. 6A to 6C are views for describing another example of the circumferential length detection process applied for the present embodiment of the present invention.
Figure 6B:
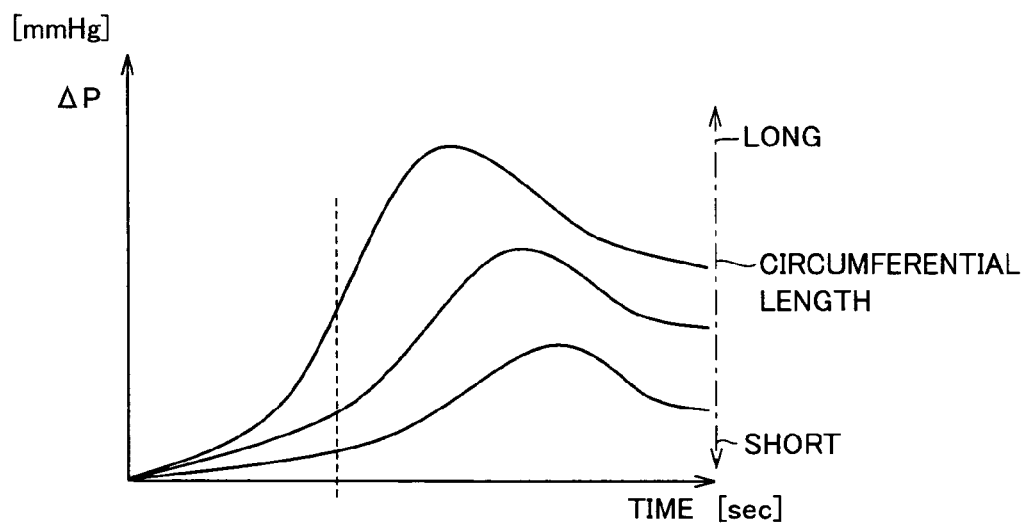
Figure 6C:
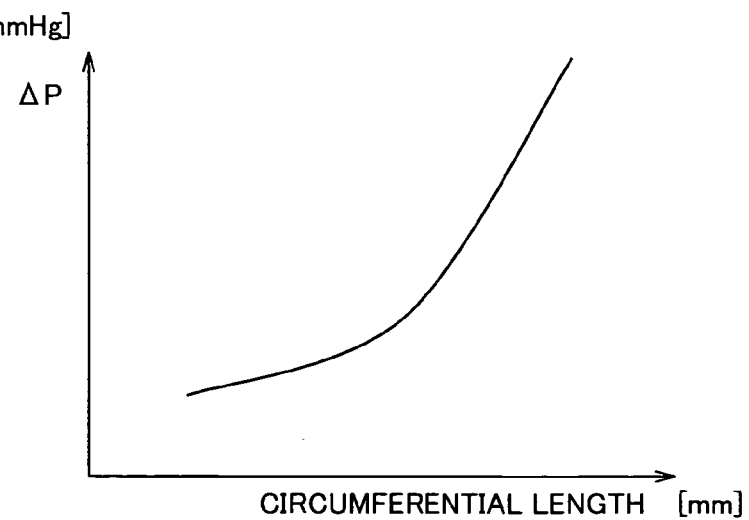

With reference to FIG. 6A to FIG. 6C, there will be described a process for identifying (detecting) the circumferential length of the region for measurement from the relative variation ΔP in cuff pressure Pc since the start of winding, at an arbitrary predetermined time during the cuff winding process after the completion of pre-pressurization (=the difference between the cuff pressure Pc at the completion of pre-pressurization and the cuff pressure Pc at a predetermined time). In FIG. 6A and FIG. 6B, there are illustrated the variations in cuff pressure Pc and in the variation ΔP in relation to the circumferential length of the region for measurement designated by a dashed line.

In FIG. 6A, similarly to in FIG. 5A, the vertical axis represents cuff pressure Pc and the horizontal axis represents the time elapsed since the completion of pre-pressurization, in cuff winding. In FIG. 6B, there is shown the relationship between the cuff-pressure variation ΔP and the elapsed time in the cuff winding, depending on the longer (or the shorter) the circumferential length of the region for measurement (depending on the thickness of the arm). FIG. 6C illustrates the relationship between the cuff-pressure variation ΔP since the completion of pre-pressurization at a predetermined time designated by a broken line in FIG. 6B and the circumferential length of the region for measurement. According to FIG. 6C, the circumferential length of the region for measurement can be determined based on the relative cuff-pressure variation ΔP since the start of winding at the predetermined time.

It is assumed that information indicating the relationship of FIG. 6C is acquired in advance by experiments and is prestored in memory 39 as a table 392.

CPU 30 measures, using timer 301 therein, an arbitrary time since the start of winding, and then calculates the cuff pressure variation ΔP at the time point. Then, based on the calculated cuff-pressure variation ΔP, CPU 30 identifies a corresponding circumferential length of the region for measurement by searching table 392 in memory 39 and reads out it therefrom. Thus, the circumferential length of the region for measurement of the subject can be detected.

While the circumferential length of the region for measurement is detected by searching table 392 herein, the circumferential length of the region for measurement may be calculated using an equation representing the relationship of FIG. 6C.

(Switching of Blood-Pressure Calculation Processes)

First to third exemplary blood-pressure value calculation processes will be described.

(First Exemplary Process Switching)

FIG. 1B illustrates the general processes in the first exemplary switching. There are prepared several types of processes as the blood pressure calculation process in step ST5 in FIG. 1A. In the first exemplary process switching, a process of type selected according to the circumferential length of the region for measurement determined in step ST1 is employed, out of the several types of processes.

At first, the circumferential length of the region for measurement determined in step ST1 is discriminated (step ST50). For example, when the circumferential length of the region for measurement is "a", a blood-pressure calculation process appropriate for the circumferential length "a" is selected and executed (step ST51). When the circumferential length of the region for measurement is "b", another blood-pressure calculation process (step ST52) appropriate for it is selected and executed. When the circumferential length of the region for measurement is "n", a further blood-pressure calculation process (step ST5$n$) appropriate for it is selected and executed.

The processes in steps ST51 to 5$n$ are prestored in memory 39 as programs and CPU 30 reads out a program from memory 39, thus achieving selection and switching. Therefore, blood pressures can be measured with high accuracy, regardless of the circumferential length of the region for measurement.

(Second Exemplary Process Switching)

While the program to be executed by CPU 30 is switched in the aforementioned first exemplary process switching, the values of characteristic amounts referred in a blood-pressure calculation algorism (program) may be selectively switched according to the circumferential length of the region for measurement.

For example, a blood pressure can be calculated using characteristic amounts in a waveform representing the variation of the amplitude value of a pulse wave signal depending on the cuff pressure Pc. The process of the calculation is illustrated in FIG. 1C. More specifically, it is known that a systolic blood pressure and a diastolic blood pressure can be detected at the points at which the pulse-wave amplitudes are at predetermined percentages of the maximum pulse-wave amplitude of the pulse wave amplitude waveform in FIG. 7. According to FIG. 7, the diastolic blood pressure can be detected as the cuff pressure Pc at which the pulse-wave amplitude is the maximum pulse-wave amplitude×β% and the systolic blood pressure can be detected as the cuff pressure Pc at which the pulse-wave amplitude is the maximum pulse-wave amplitude×α%. In FIG. 1C, the values of variables α and β are changed according to the circumferential length of the region for measurement acquired in step ST1 (step ST501), wherein the variables α and β are characteristic amounts of the waveform representing the variation of the amplitude value of the pulse wave signal. Thus, blood pressures can be measured with high accuracy, regardless of the circumferential length of the region for measurement (step ST502).

(Third Exemplary Process Switching)

While the process is switched at the start of blood pressure calculation or during the calculation in the first or second exemplary process switching, the result of calculation may be corrected using parameter values appropriate for the circumferential length of the region for measurement after the blood pressure calculation, as will be described in the third exemplary process switching. For example, the result of calculation may be corrected by weighting with a proportionality constant, etc., appropriate for the circumferential length of the region for measurement. This correction is executed in step ST5a in FIG. 1A.

Also, it is possible to employ combinations of any of the selective switching of blood pressure measurement algorisms based on the circumferential length of the region for measurement according to the first exemplary process switching, the selective switching of characteristic amounts for the blood pressure measurement algorism based on the circumferential length of the region for measurement according to the second exemplary process switching, and the correction appropriate for the circumferential length of the region for measurement after blood pressure calculation according to the third exemplary process switching.

(Other Embodiments)

While the circumferential length of the region for measurement is utilized only for correcting the blood pressure calculation process in the aforementioned embodiments, it may be utilized for correcting the control of pressurization of blood-pressure measurement bladder 50 in step ST2 and the control of depressurization of blood-pressure measurement bladder 50 in step ST3, as in FIG. 8A and FIG. 8B, FIG. 9A and FIG. 9B and FIG. 10A and FIG. 10B. Namely, in order to calculate blood pressures, the cuff pressure of blood-pressure measurement bladder 50 may be adjusted according to an adjustment parameter value appropriate for on the detected circumferential length of the region for measurement. This enables optimum control of the pressurization or depressurization according to the circumferential length of the region for measurement, resulting in improvement of the accuracy of blood-pressure calculation.

Reference is made to table 393 prestored in memory 39 for optimal control of pressurization according to the circumferential length of the region for measurement, while reference is made to table 394 prestored in memory 39 for optimum control of depressurization according to the circumferential length of the region for measurement. It is assumed that data of table 393 and table 394 are acquired in advance by experiments.

In table 393, there is stored data of the levels of voltages to be supplied to pump 33 in correspondence with the respective values of plural circumferential lengths of the region for measurement. Here, the operation of pump 33, namely the adjustment of pressurization rate, is controlled with the level of the voltage supplied to pump 33. However, this may be achieved as follows. Namely, the time period in which a voltage applied to pump 33 may be controlled with PWM (Pulse Width Modulation). In this case, data of pulse widths is stored in table 393 in correspondence with the respective values of plural circumferential lengths of the region for measurement. Further, in table 394, there is stored data of the levels of voltages to be supplied to valve 34 in correspondence with the respective values of plural circumferential lengths of the region for measurement. Here, the operation of valve 34, namely the adjustment of depressurization rate, is controlled with the level of the voltage supplied to valve 34. However, this may be achieved as follows. Namely, the time period in which a voltage is applied to valve 34 may be controlled with PWM (Pulse Width Modulation). In this case, data of pulse widths is stored in table 394 in correspondence with the respective values of plural circumferential lengths of the region for measurement.

Therefore, by searching table 393 or 394 based on the detected circumferential length of the region for measurement, it is possible to acquire data of a corresponding voltage level or data of a corresponding voltage application time period.

(Pressurization Rate Adjustment According to Circumferential Length of Region for Measurement)

In pressurization of blood-pressure measurement bladder 50, a parameter value used for the control of pressurization is changed based on the circumferential length of the region for measurement. Here, the voltage level for driving pump 33 is corrected based on the circumferential length of the region for measurement, and the voltage at the corrected level is applied to pump 33, thus realizing optimum control of pressurization, regardless of the circumferential length of the region for measurement.

Figure 8A:
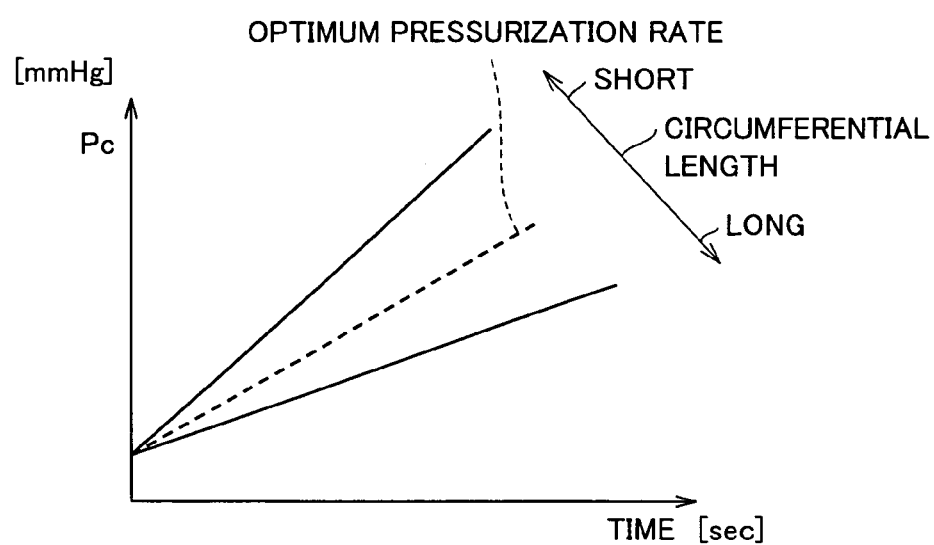
FIGS. 8A and 8B are views for describing the process of pressurization rate adjustment according to the circumferential length of the region for measurement.
Figure 8B:
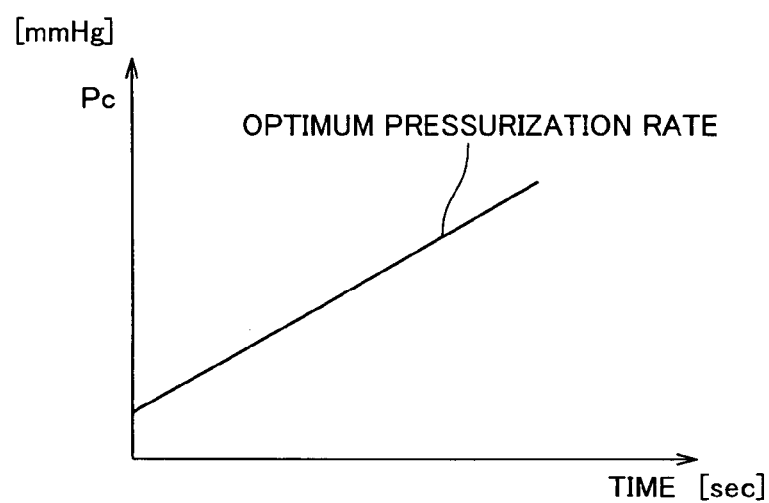

With reference to FIG. 8A and FIG. 8B, there will be described a process for adjusting the pressurization rate for blood-pressure measurement bladder 50 depending on the circumferential length of the region for measurement. In FIG. 8A, there is illustrated the variation of cuff pressure Pc in relation to the circumferential length of the region for measurement designated by a solid line arrow. In the cuff pressurization in step ST2, when the level of the voltage supplied to pump 33 from pump driving circuit 36 for driving pump 33 is maintained constant regardless of the circumferential length of the region for measurement, the pressurization rate will be lower in the case where the circumferential length is larger or longer (the arm is thicker) while the pressurization rate will be higher in the case where the circumferential length is smaller or shorter (the arm is thinner), as compared with an optimum pressurization rate (cuff-pressure rising rate) designated by a broken line, as illustrated in FIG. 8A.

As described above, when the same level of voltage is supplied to pump 33 for driving it, the pressurizing time period varies depending on the circumferential length of the region for measurement, since the time period required for achieving an optimal pressurization condition for blood pressure measurements varies depending on the circumferential length of the region for measurement. This will prevent accurate detection of the signals of pulse waves superimposed on the cuff pressure or put stress on the subject, which may be factors of obstruction to accurate blood-pressure measurements.

Therefore, in order to enable accurately detecting the signal of pulse waves superimposed on the cuff pressure in the pressurization process and prevent excessive stress to be put on the subject, thus improving the accuracy of blood pressure measurements, it is necessary that the pressurization rate is adjusted, namely the voltage level for driving pump 33 is selectively switched, based on the acquired circumferential length of the region for measurement.

Figure 9A:
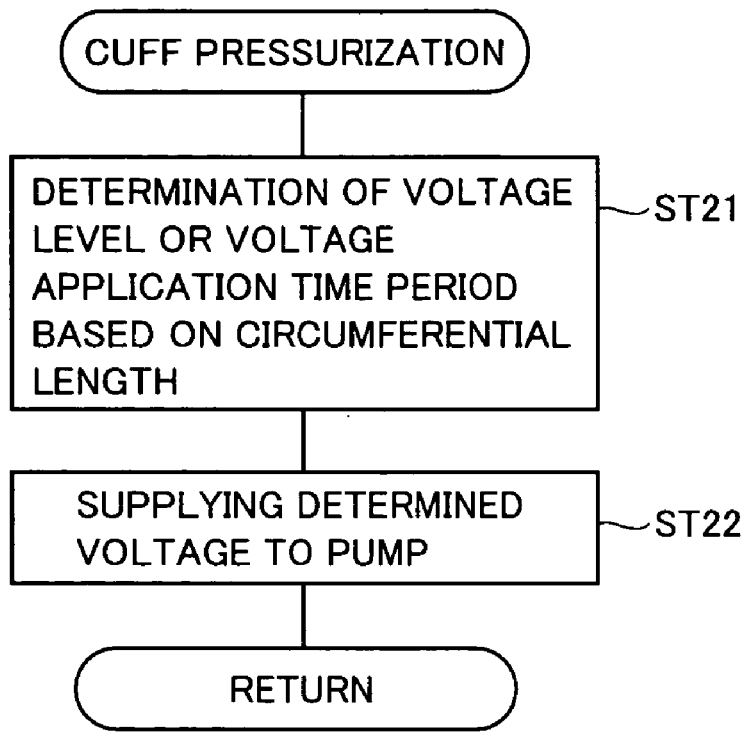
FIGS. 9A and 9B are process flowcharts of the cuff pressurization and the cuff depressurization according to the present embodiment of the present invention.

Therefore, in the process of FIG. 9A, in order to make the pressurization rate in step ST2 to be the optimum pressurization rate as illustrated by the broken line in FIG. 8A, table 393 is searched based on the circumferential length of the region for measurement acquired in step ST1 and, based on the result of the searching, the level or the application time period of the driving voltage, which is the adjustment parameter value, is determined (step ST21). Then, a driving voltage is supplied to pump 33 according to the determined level or application time period (step ST22). As a result, the pressurization rate is made to be the optimum pressurization rate as illustrated in FIG. 8B, regardless of the circumferential length of the region for measurement. This enables accurately detecting the signal of pulse waves superimposed on the cuff pressure in the pressurization process and prevents excessive stress to be put on the subject, thus enabling accurate blood pressure measurements.

(Depressurization Rate Adjustment According to Circumferential Length of Region for Measurement)

In depressurization of blood-pressure measurement bladder 50, a parameter value used for the control of depressurization is changed based on the circumferential length of the region for measurement. Here, the voltage level for driving valve 34 is corrected based on the circumferential length of the region for measurement, and the voltage at the corrected level is applied to valve 34, thus realizing optimum control of depressurization, regardless of the circumferential length of the region for measurement.

Figure 10A:
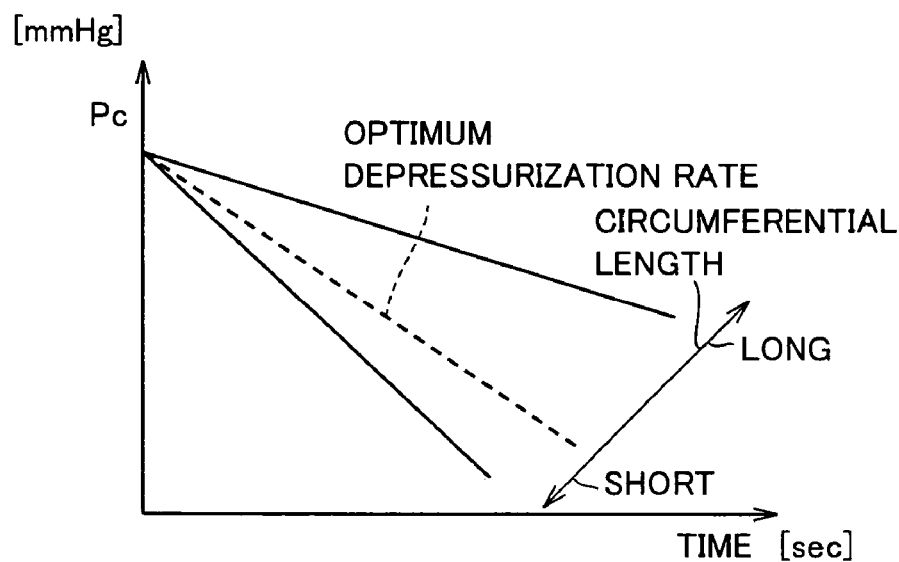
FIGS. 10A and 10B are views for describing the process of depressurization rate adjustment according to the circumferential length of the region for measurement.
Figure 10B:
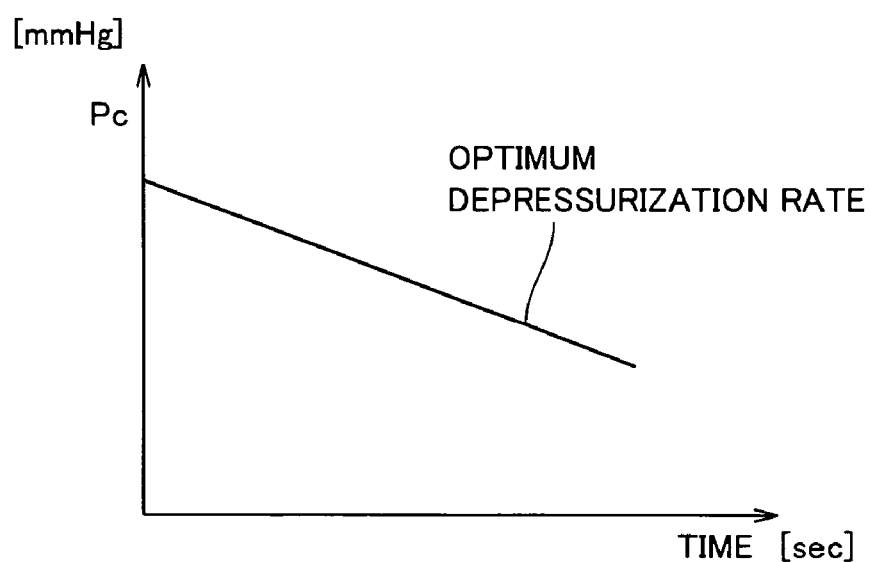

With reference to FIG. 10A and FIG. 10B, there will be described a process for adjusting the depressurization rate for blood-pressure measurement bladder 50 depending on the circumferential length of the region for measurement. In FIG. 10A, there is illustrated the variation of cuff pressure Pc in relation to the circumferential length of the region for measurement designated by a solid line arrow. In the cuff depressurization in step ST3, when the level of the voltage supplied to valve 43 from valve driving circuit 37 in order to drive valve 43 for opening it is maintained constant regardless of the circumferential length of the region for measurement, the depressurization rate will be lower in the case where the circumferential length is larger or longer (the arm is thicker) while the depressurization rate will be higher in the case where the circumferential length is smaller or shorter (the arm is thinner), as compared with an optimum depressurization rate (cuff-pressure decreasing rate) designated by a broken line, as illustrated in FIG. 10A.

As described above, when the same level of voltage is supplied to valve 34 in order to drive valve 34 for opening it, the depressurizing time period varies depending on the circumferential length of the region for measurement, since the time period in which an optimum depressurization condition (slow deflating condition) is maintained varies depending on the circumferential length of the region for measurement. This will prevent accurate detection of the signals of pulse waves superimposed on the cuff pressure or put stress on the subject, which may be factors of obstruction to accurate blood-pressure measurements.

Therefore, in order to enable accurately detecting the signal of pulse waves superimposed on the cuff pressure in the pressurization process and prevent excessive stress to be put on the subject, thus improving the accuracy of blood pressure measurements, it is necessary that the depressurization rate is adjusted, namely the voltage level or the voltage application time period for driving valve 34, which is the adjustment parameter, is selectively switched, based on the acquired circumferential length of the region for measurement.

Figure 9B:
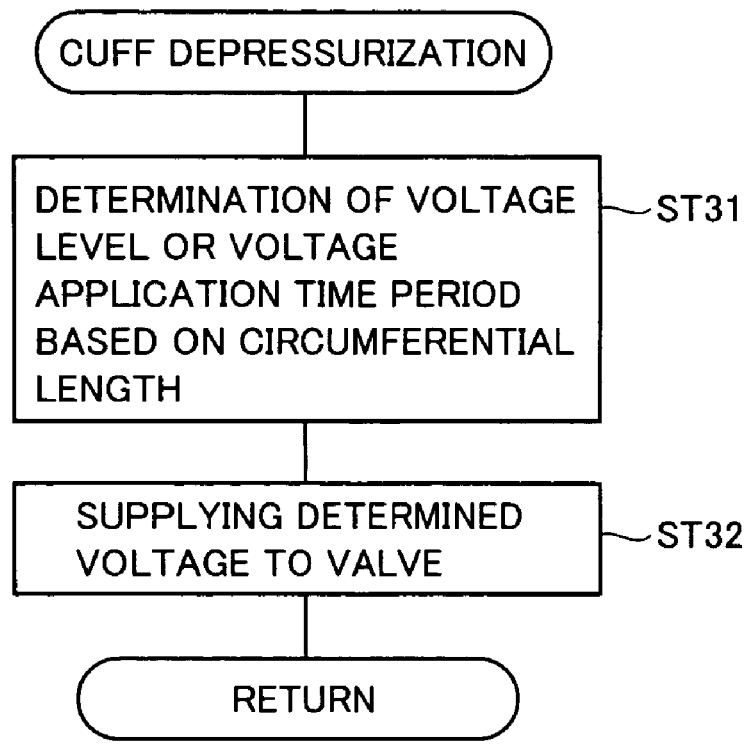

Therefore, in the process of FIG. 9B, in order to make the depressurization rate in step ST3 to be the optimum depressurization rate as illustrated by the broken line in FIG. 9A, table 394 is searched based on the circumferential length of the region for measurement acquired in step ST1 and, based on the result of the searching, the level or the application time period of the driving voltage is determined (step ST31). Then, a driving voltage is supplied to valve 34 according to the determined level or application time period (step ST32). As a result, the depressurization rate is made to be the optimum pressurization rate as illustrated in FIG. 9B, regardless of the circumferential length of the region for measurement. This enables accurately detecting the signal of pulse waves superimposed on the cuff pressure and prevents excessive stress to be put on the subject, thus enabling accurate blood pressure measurements.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An electronic blood pressure measurement device comprising:
   a measurement bladder which is inflated when supplied with fluid and is configured to be wound around a region for blood pressure measurement;
   a pressure detection portion detecting the pressure in said measurement bladder;
   a circumferential length detection portion detecting the circumferential length of said region based on a relative variation in the pressure detected by said pressure detection portion during winding said measurement bladder around said region after a predetermined amount of said fluid has been supplied to and enclosed in said measurement bladder;
   a blood pressure calculation portion calculating a blood pressure value based on said pressure detected by said pressure detection portion according to said circumferential length of said region detected by said circumferential length detection portion.

2. The electronic blood pressure measurement device according to claim 1, wherein
   said blood pressure calculation portion calculates a blood pressure value based on the pressure in said measurement bladder according to a process selected based on said circumferential length detected by said circumferential length detection portion out of a plurality of processes for calculating said blood pressure value.

3. The electronic blood pressure measurement device according to claim 1, wherein
   said blood pressure calculation portion calculates a blood pressure value based on the pressure detected by said pressure detection portion according to characteristic amounts for calculating a blood pressure value selected based on said circumferential length detected by said circumferential length detection portion.

4. The electronic blood pressure measurement device according to claim 1, wherein
   said blood pressure calculation portion corrects the calculated blood pressure value using a correction parameter value appropriate for said circumferential length detected by said circumferential length detection portion.

5. The electronic blood pressure measurement device according to claim 1, further comprising;
   a pressure adjustment portion adjusting the pressure in said measurement bladder for calculating said blood pressure value, wherein
   said pressure adjustment portion adjusts the pressure in said measurement bladder according to an adjustment parameter value according to said circumferential length detected by said circumferential length detection portion.

6. A blood pressure measurement device comprising:
   a measurement bladder that is inflated when supplied with fluid and is configured to be wound around a region for blood pressure measurement;
   a pressure detection portion detecting pressure in said measurement bladder;

a circumferential length detection portion detecting the circumferential length of said region during winding said measurement bladder around said region after a predetermined amount of said fluid has been supplied to and enclosed in said measurement bladder; and a blood pressure calculation portion calculating a blood pressure value based on said pressure detected and said circumferential length of said region, wherein said circumferential length detection portion detects the circumferential length of said region based on the time period required for raising to a predetermined value the difference between; (1) the pressure detected by said pressure detection portion when said measurement bladder is wound around said region after said predetermined amount of fluid has been enclosed in said measurement bladder; and (2) the pressure which is sequentially detected by said pressure detection portion during further winding said measurement bladder around said region.

7. The electronic blood pressure measurement device according to claim 6, wherein said predetermined value is a value indicating a state where said measurement bladder has been optimally wound around said region.

8. A blood pressure measurement device comprising:

a measurement bladder that is inflated when supplied with fluid and is configured to be wound around a region for blood pressure measurement;

a pressure detection portion detecting pressure in said measurement bladder;

a circumferential length detection portion detecting the circumferential length of said region during winding said measurement bladder around said region after a predetermined amount of said fluid has been supplied to and enclosed in said measurement bladder; and a blood pressure calculation portion calculating a blood pressure value based on said pressure detected and said circumferential length of said region, wherein said circumferential length detection portion detects the circumferential length of said region based on the difference between: (1) the pressure detected by said pressure detection portion when said measurement bladder is wound around said region after said predetermined amount of fluid has been enclosed in said measurement bladder; and (2) the pressure detected by said pressure detection portion when a predetermined time period has elapsed since the start of further winding of said measurement bladder around said region.

9. A method for measuring blood pressure by winding a measurement bladder, which is inflated when supplied with fluid, around a region, said method comprising;

detecting the circumferential length of said region based on a relative variation in the pressure in said measurement bladder during winding said measurement bladder around said region after a predetermined amount of fluid is supplied to and enclosed in said measurement bladder; and calculating a blood pressure value based on the pressure in said measurement bladder, according to said circumferential length detected.

* * * * *